United States Patent [19]
Gilberg

[11] Patent Number: 5,366,449
[45] Date of Patent: Nov. 22, 1994

[54] MALE EXTERNAL CATHETER ASSEMBLY AND METHOD

[76] Inventor: Samuel L. Gilberg, 2900 Ossenfort Rd., Glencove, Mo. 63038

[21] Appl. No.: 33,159

[22] Filed: Mar. 16, 1993

[51] Int. Cl.$^5$ ............................................. A61F 5/44
[52] U.S. Cl. ................................... 604/349; 604/351; 128/844
[58] Field of Search ........................... 604/349–352; 128/842, 843, 844, 761; 4/144.1–144.21

[56] References Cited

U.S. PATENT DOCUMENTS

| | | | |
|---|---|---|---|
| 2,379,346 | 6/1945 | Farrell | 604/351 |
| 3,721,243 | 3/1973 | Hesterman et al. | 604/353 |
| 4,020,843 | 5/1977 | Kanall | 604/351 |
| 4,239,044 | 12/1980 | Pavlinch | 604/352 |
| 4,553,968 | 11/1985 | Komis | 604/353 |
| 5,009,649 | 4/1991 | Goulter et al. | 604/349 |
| 5,032,118 | 7/1991 | Mason | 604/349 |
| 5,195,997 | 3/1993 | Carns | 604/349 |

*Primary Examiner*—Randall L. Green
*Assistant Examiner*—Rob Clarke
*Attorney, Agent, or Firm*—Frank L. Kubler

[57] ABSTRACT

A male external catheter assembly for transporting and containing urine includes a condom having a discharge end and having a discharge port at the discharge end, a discharge tube having a tube first end and a tube second end, the tube first end being sealingly secured to the condom discharge end, a urine receiving vessel at the tube second end, a garment having a condom passing opening, a condom masking sleeve having a sleeve first end and a sleeve second end, the sleeve first end being positioned adjacent to the condom passing opening and substantially surrounding the condom discharge end for concealing the condom. The condom masking sleeve preferably includes a condom inspection slit and the condom preferably has an off-center discharge port at its tip. A method of male catheterization for a user wearing a garment having a condom passing opening includes the steps of fitting a condom having a discharge port onto the user's penis, extending the condom through the condom passing opening, extending a free end of a discharge tube extending from said discharge port to discharge urine into a urine collection vessel. The method may additionally include the step of placing a condom masking sleeve over the condom, outside the condom passing opening, to conceal the condom. The method may further include the steps of removing the discharge tube from the condom discharge port, and inserting a plug into the discharge port to prevent urine leakage from the condom.

18 Claims, 4 Drawing Sheets

FIG. I

MALE EXTERNAL CATHETER ASSEMBLY AND METHOD

BACKGROUND OF THE INVENTION

1. Field of the Invention

The present invention relates generally to the field of catheters, and more specifically to male external catheter assembly for collecting large quantities of urine while remaining inconspicuous and unobstructed, including a catheter condom having a flanged discharge port at its tip, a discharge tube having two ends, one end fitting snugly and sealingly over the flanged discharge port, the other end fitting over a flanged entrance port in the lid of a urine collection bottle, a pair of trousers having a trouser opening below the conventional fly opening through which the condom extends to help prevent the tube from bending and kinking, a condom mask in the form of a fabric sleeve fitting around the protruding end of the condom and attached at one end to the edges of the trouser opening, the second end of the condom mask having an axial slit which can be opened by the user to inspect the condom and tube connection; the condom mask optionally being removable from the trouser opening; the condom mask, tube and bottle preferably being colored to blend in with the trouser or chair material and not be noticeable, the discharge tube preferably being made of kink-resistant vinyl, the assembly including tapered tissue paper plugs to insert into the discharge port to prevent leakage when the discharge tube is disconnected from the condom.

2. Description of the Prior Art

There have long been catheters for incontinent or physically restricted male and female users for carrying urine to a receiving bag. The receiving bag is usually a pouch or bottle and is typically attached to the user's leg with leg bag straps. The catheters for male users incorporate a condom having a flanged port at its tip to which a urine discharge tube is attached. The tube extends down inside the trouser leg.

Problems with these prior male catheters include the tendency of the tube to bend sharply relative to the condom, kink inside the trousers and obstruct urine flow, often causing urine back-up and leakage. The condom can also kink. Another problem is that the bag attached to the leg can have only a limited capacity due to trouser leg width, and this capacity is not sufficient for many long duration uses. Another problem is that the weight of a full leg bag can cause the leg bag straps to act like a tourniquet, slowing blood circulation in that part of the leg. A full bag can at the same time cause considerable discomfort, and can sag and become visible below the trouser leg cuff.

Examples of prior catheters fitting this general description and having the identified problems include the TEXAS CATHETER TM and UNI-DRAIN TM male external catheters. These are illustrated on page 53 of the St. Louis Medical Supply, 1990 Catalog. They also include the BARD TM catheters, the HOLLISTER TM catheters on page 42, UNITED WEIMER TM on page 45, the CONVEEN TM, COLOPLAST TM, PHARMASEAL TM and MCGAW TM catheters on page 43 and the BARDIA TM, DOW TM, CURITY TM, SIERRA TM and CONVATEC TM catheters on page 48 of the St. Louis Medical Supply 1990 catalog.

To seal the condom discharge opening after the discharge tube is disconnected, prior catheters have relied on plastic or metal clamps to crimp and close the opening flange. Problems with these clamps include that they are bulky, can irritate, and can be hard to manipulate to attach and detach.

It is thus an object of the present invention to provide a male external catheter assembly which minimizes kinking of the condom and of the urine discharge tube so that obstruction and leakage are minimized.

It is another object of the present invention to provide such a catheter assembly which positions the condom for natural and comfortable urine discharge while keeping the condom completely hidden, and to provide a damless condom which minimizes kinking.

It is still another object of the present invention to provide such a catheter assembly which provides substantial urine storage capacity and thus eliminates the worry of overflow and back-up.

It is finally an object of the present invention to provide such a catheter assembly which has these above-recited advantages and yet is comparable in production cost to existing catheters.

SUMMARY OF THE INVENTION

The present invention accomplishes the above-stated objectives, as well as others, as may be determined by a fair reading and interpretation of the entire specification.

A male external catheter assembly is provided for transporting and containing urine, including a condom having a discharge end and having a discharge port at the discharge end, a discharge tube having a tube first end and a tube second end, the tube first end being sealingly secured to the condom discharge end, a urine receiving vessel at the tube second end, a garment having a condom passing opening, a condom masking sleeve having a sleeve first end and a sleeve second end, the sleeve first end being positioned adjacent to the condom passing opening and substantially surrounding the condom discharge end for concealing the condom. The condom masking sleeve preferably includes a condom inspection slit. The inspection slit preferably extends essentially axially from the sleeve second end toward the sleeve first end. The sleeve first end may be removably attached to the condom passing opening with an attachment mechanism. The sleeve first end may alternatively be permanently attached to the condom passing opening with an attachment mechanism. The condom masking sleeve is preferably colored to match a nearby item to be visually less conspicuous. Where the garment is a pair of trousers, the condom passing opening is located below the conventional trouser fly opening location.

A male external catheter assembly is also provided for transporting and containing urine, including a condom having a discharge end and having a discharge port at the discharge end, a discharge tube having a tube first end and a tube second end, the tube first end being sealingly secured to the condom discharge end, a urine receiving vessel at the tube second end, a garment having a condom passing opening, and a port plug for inserting into the condom discharge port for preventing urine leakage. The port plug is preferably absorbent, essentially elongate and conical, and formed of tissue paper. The plug may be formed of a sheet of tissue paper twisted into a conical shape.

A method of male catheterization is provided for a user wearing a garment having a condom passing opening, including the steps of fitting a condom having a discharge port onto the user's penis, extending the condom through the condom passing opening, extending a free end of a discharge tube extending from said discharge port to discharge urine into a urine collection vessel. The method may additionally include the step of placing a condom masking sleeve over the condom, outside the condom passing opening, to conceal the condom. The method may further include the steps of removing the discharge tube from the condom discharge port, and inserting a plug into the discharge port to prevent urine leakage from the condom.

A catheter condom is provided, including a tubular portion having a tubular wall and a longitudinal axis, a walled end of the tubular portion, and a discharge port in the walled end where the discharge port is offset in position from the longitudinal axis and toward a point on the tubular wall. The portion of the condom between the end of the penis and the discharge port is preferably formed of material which is stiffer than the condom material surrounding the penis to reduce condom kinking potential.

An apparatus is also provided for holding a garment cuff in position, including a strap for wrapping around an end of a human appendage having two ends connected to opposing points on the cuff. At least one end is preferably secured to the cuff at one point with a clip.

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figure 1:
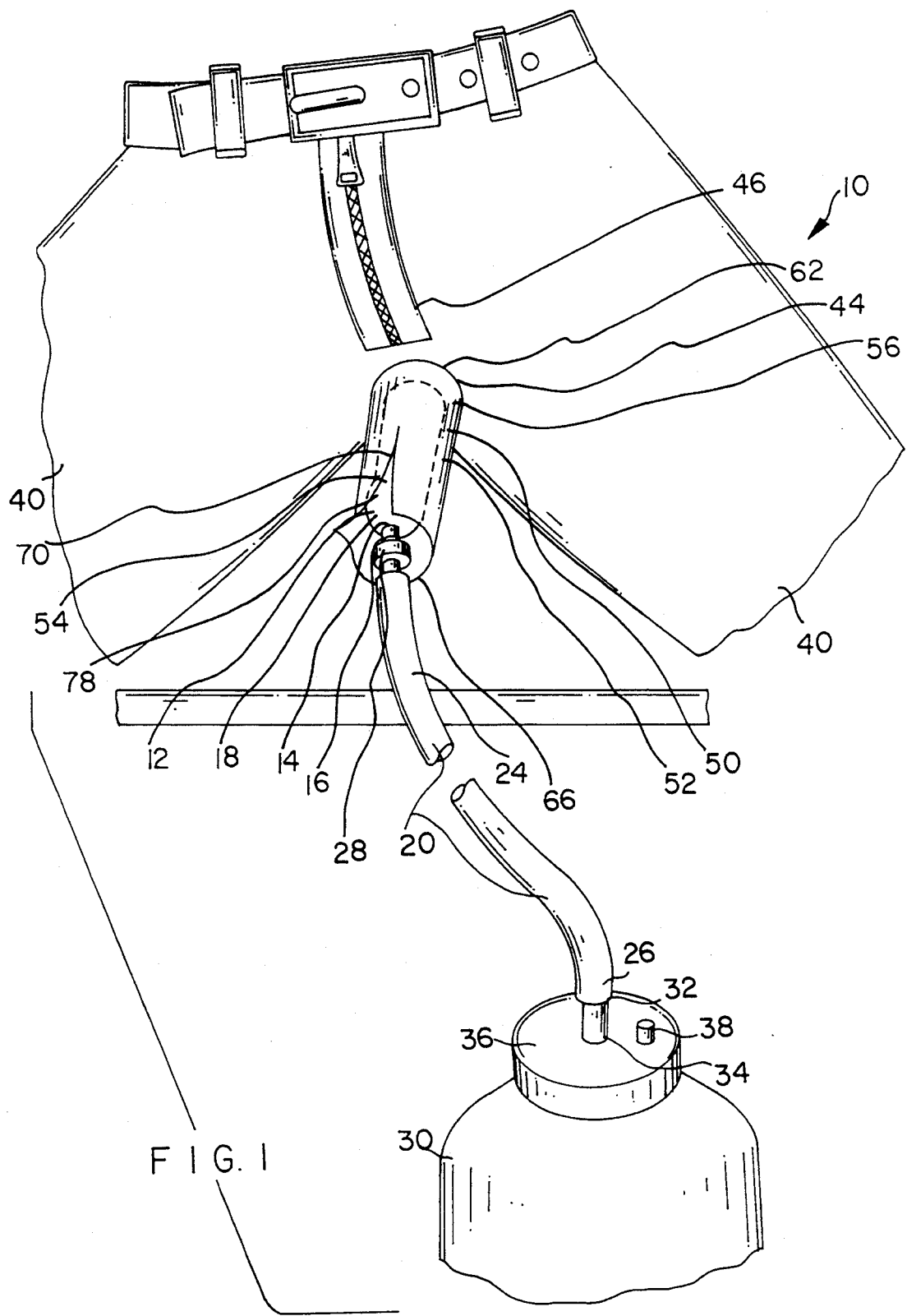
FIG. 1 is a perspective view of the inventive catheter apparatus, illustrating the condom mask with the inspection slit partly opened.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGS. are designated by the same reference numerals.

First Preferred Embodiment

Referring to FIG. 1, a male external catheter assembly 10 is disclosed for collecting large quantities of urine while remaining hidden and unobstructed. Catheter assembly 10 includes a catheter condom 12 having a discharge port 14 with a port flange 16 at its tip 18, and a discharge tube 20 having a first end 24 and a second end 26. First end 24 of tube 20 is fit snugly and sealingly over a standard connector 28 leading to port flange 16. A urine collection bottle 30 for receiving the urine is placed beside the user's bed, or mounted onto a wheel chair or a motorized cart. Discharge tube 20 second end 26 snugly and sealingly is secured to flange 32 surrounding an entrance port 34 in a lid 36 on bottle 30. Bottle 30 may include a venting port 38 in lid 36.

A garment such as a pair of trousers 40 is provided which has a condom passing trouser opening 44 below the conventional fly opening 46 through which condom 12 extends. This protruding condom arrangement prevents the trouser wall from bending tube 20 substantially out of alignment with the axis of condom 12 and thereby kinking and closing tube 20.

A condom mask 50 includes a sleeve 52 which fits around the remote end 54 of condom 12 protruding through trouser opening 44. Sleeve 52 is made of a fabric or other suitable flexible material, and has a first sleeve end 56 which is attached to the edges 62 of trouser opening 44. Sleeve end 56 can be permanently attached to edges 62 with stitches or an equivalent securing device. Sleeve end 56 can alternatively be removably attached to edges 62 with a hook and loop fastener such as VELCRO TM or with an equivalent fastener. Sleeve 52 includes a second sleeve end 66 and an inspection slit 70 which extends from second sleeve end 66 axially along a segment of sleeve 52. Inspection slit 70 can be opened by the user to inspect the condom 12 and tube 20 connection. Slit 70 is preferably located on the underside of sleeve 52 and the top portion of sleeve second end 66 is lifted to inspect. Condom 12 may be either a re-usable or a disposable condom such as that sold by MENTOR TM. Condom mask 50, tube 20 and bottle 30 are preferably tinted, painted or otherwise colored to blend in with the trouser or chair material or chair frame colors to be inconspicuous. Mask 50, tube 20 and bottle 30 may also carry labels indicating they are for another purpose, once again to conceal their actual function. Bottle 30 may also be hidden inside a waste paper basket. Discharge tube 20 is preferably made of kink-resistant vinyl, rubber or other suitable material, to further reduce the chances of flow obstruction. The alternative removable condom mask feature permits mask 50 to be removed for separate laundering or replacement. For this alternative, mask material may be selected which itself sufficiently engages edges 62 of opening 44, VELCRO TM engaging mask material, mating VELCRO TM sections, or a zipper at edges 62 may hold mask 50 in place. In addition, trouser opening 44 is preferably provided with closing means such as a zipper or VELCRO TM, for use when mask 50 is removed.

Figure 2:
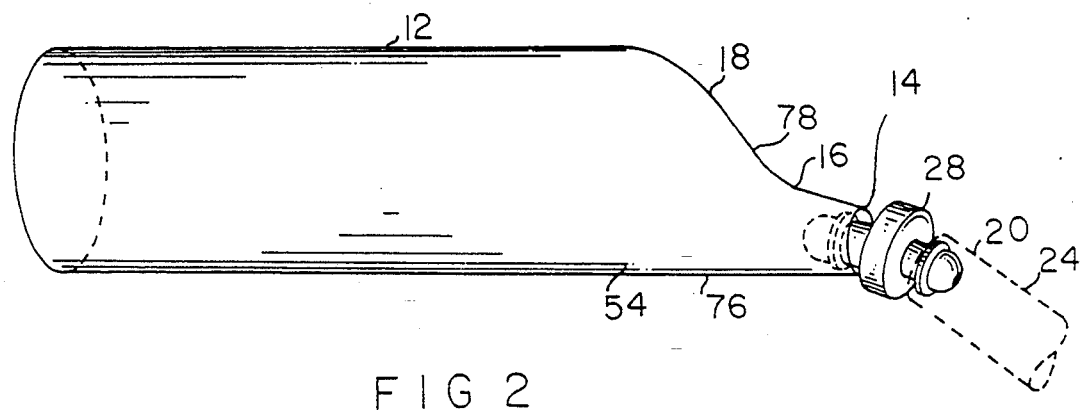
FIG. 2 is a perspective view of the inventive catheter condom having the offset discharge port for irritation and dripping upon tube disconnection. A portion of the discharge tube is shown in broken lines.

Condom 12 preferably has a discharge port 14 offset from the longitudinal axis of condom 12, so that port 14 is adjacent to the outermost side wall 76 of the condom. See FIG. 2. When in use, this damless condom 12 is rotationally positioned on the penis so that port 14 is adjacent the lowest part of condom 12 side wall 76. This design is intended to permit complete urine drainage so that minimal dripping occurs when discharge tube 20 is removed from discharge port 14. None of the urine is dammed up by the condom 12 end wall 78, but it is carried out and away by gravity, so that it does not linger and cause irritation. The portion of disharge end 54 of inventive condom 12, from the end of the penis to the remote end of discharge port 14, is preferably made of stiffer or thicker material to reduce kinking potential.

Figure 3:
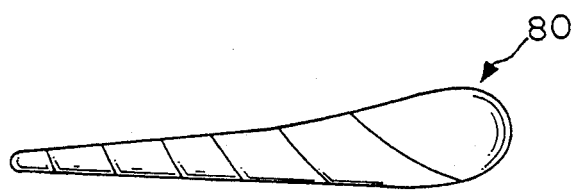
FIG. 3 is a side view of the inventive condom discharge port plug formed of a twisted sheet of tissue paper.
Figure 4:
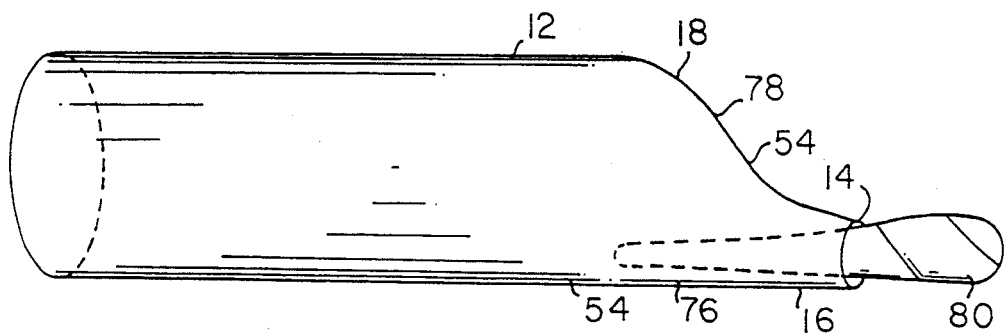
FIG. 4 is a view of the plug of FIG. 3 inserted into the discharge port of the condom of FIG. 2.

A tapered, absorbent tissue paper plug 80 is also provided for insertion into condom port flange 16 when discharge tube 20 is disconnected. See FIGS. 3 and 4. Plug 80 is preferably formed by rolling or twisting a sheet of tissue paper into an elongate conical shape, and serves to prevent urine leakage from condom 12. Plug 80 may also be formed of cotton.

Catheter apparatus 10 is well suited not only to those having related medical conditions but for anyone who sits for extended periods of time. This includes people in occupations which require prolonged sitting, such as pilots, train engineers, and people with office jobs. Bottle 30 may be of any convenient size, such as half gallon or gallon size, and rest on the floor for office use. Bottle 30 equivalently may be the size and shape of a bicycle bottle and secured to a chair leg or other furniture with VELCRO ™ strips rather than resting on the floor, such as for use in airplanes. A bicycle bottle is probably about twice the capacity of a conventional urine collection bag. In either case, problems of the prior art are avoided because the user's leg does not support bottle 30.

Figure 5:
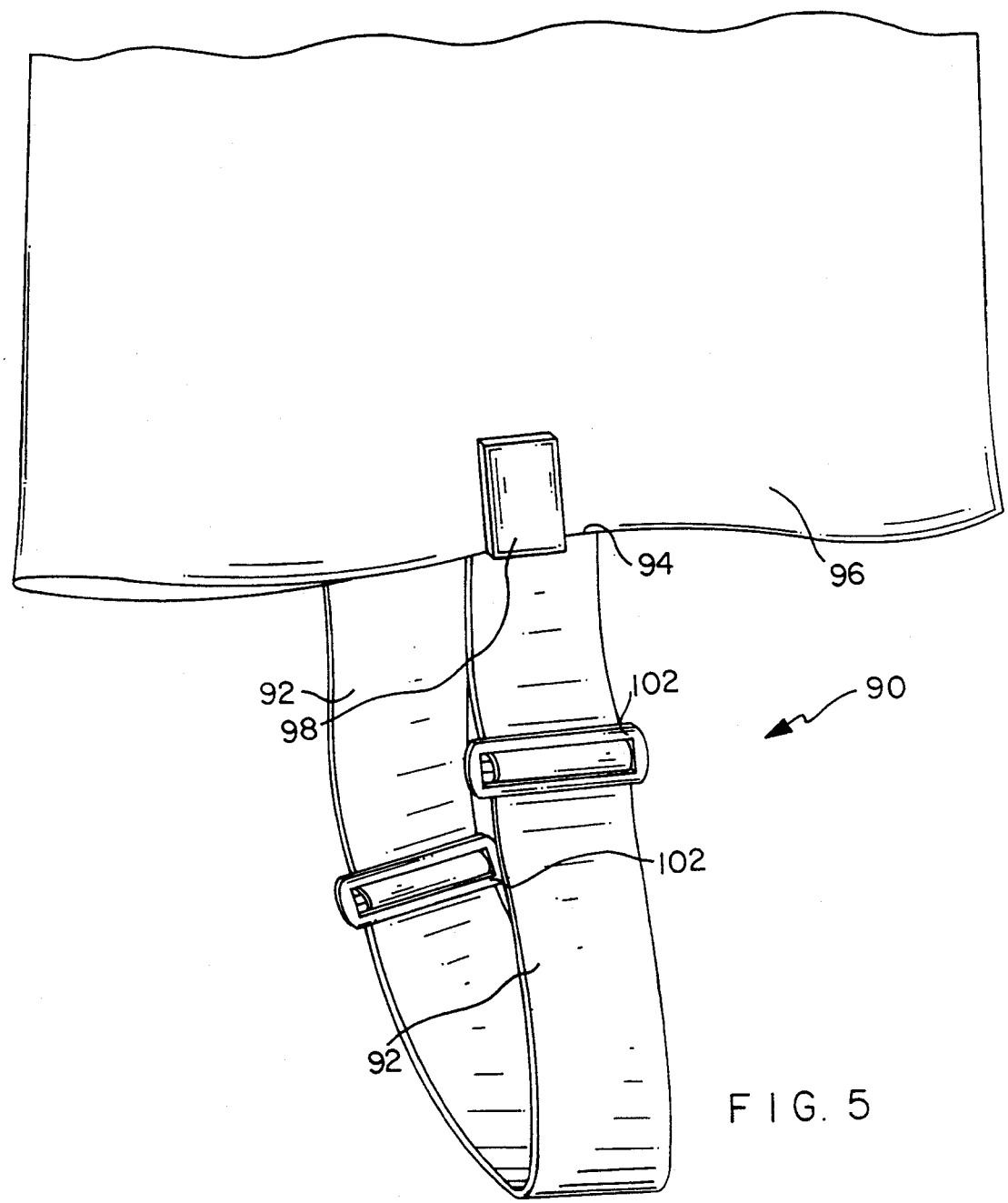
FIG. 5 is a perspective view of the inventive clip-on jodhpur secured to a garment cuff.
Figure 6:
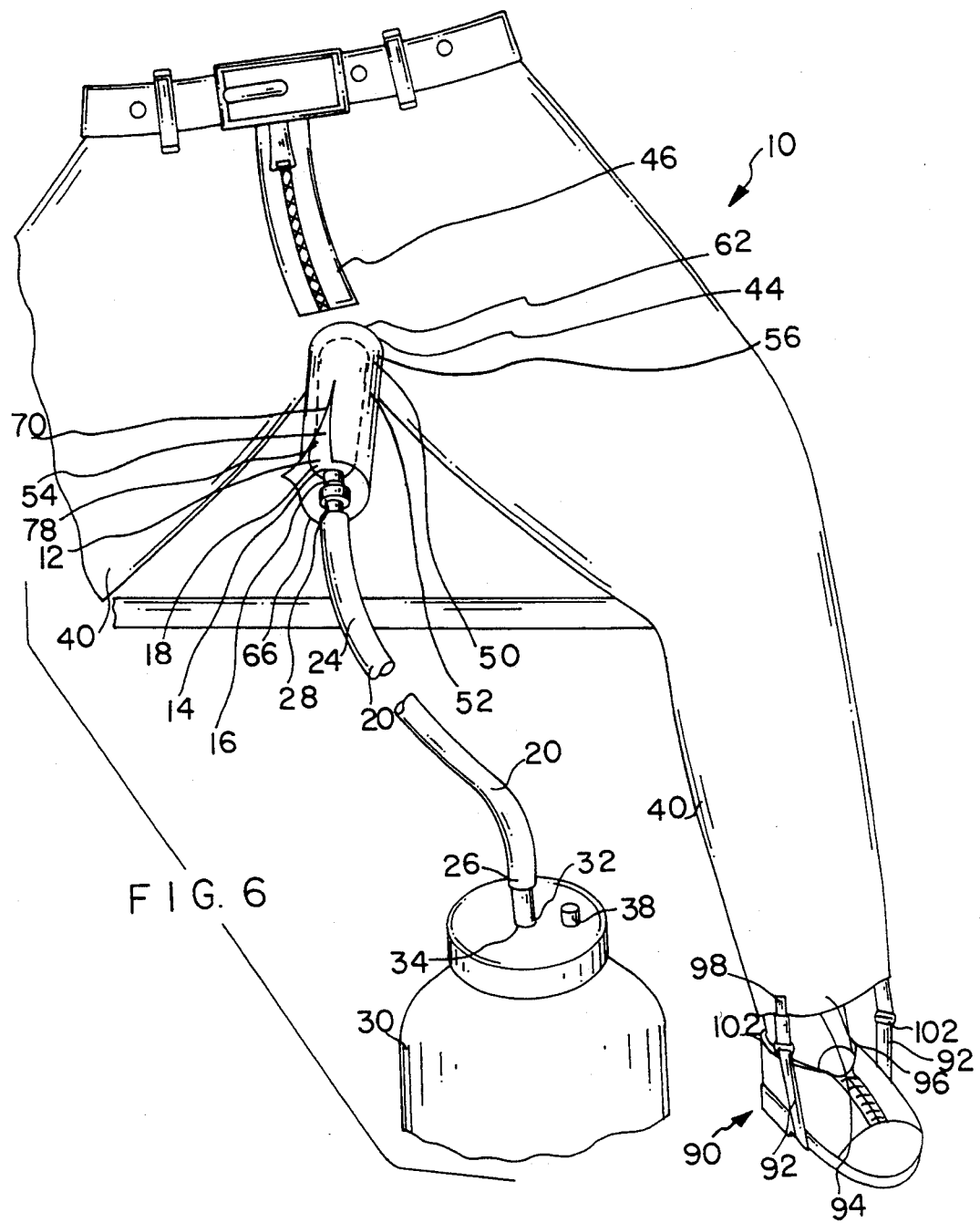
FIG. 6 is a perspective view as of FIG. 1, with the inventive jodhpur shown as part of the apparatus combination.

A clip-on jodhpur 90 is preferably used to prevent discharge end 54 of condom 12 and discharge tube 20 from kinking, and the resulting backing up of the urine and loosening of condom 12. See FIG. 6. Jodhpur 90 also prevents the trouser 40 leg from riding up on the leg and bunching up against the user's body. The inventive jodhpur 90 is a strap 92 which extends from opposing points 94 of the trouser cuff 96 at the bottom of a trouser 40 leg and elastically around the sole of the user's shoe. See FIG. 5. Clips 98 may secure strap 92 to cuff 96 and buckles 102 permit strap 92 length adjustment. A jodhpur 90 may also be used on a shirt sleeve or other cuffed garment portion for a variety of purposes.

Method

In practicing the invention, the following method may be used. Where the user is wearing trousers 40 having a trouser opening 44 below the conventional fly opening 46 location, a condom 12 having a discharge port 14 is fitted onto the user's penis. Condom 12 is extended through opening 44, and one end 24 of a discharge tube 20 is sealingly attached to discharge port 14, while the other end 26 of discharge tube 20 is positioned to discharge into a urine collection vessel 30. The method can additionally include the step of placing a condom 12 masking sleeve 52 over the condom 12 outside trouser opening 44 to conceal condom 12 from view. The method can further include the steps of removing discharge tube 20 from condom 12 discharge port 14 and inserting a plug 80 into discharge port 14 to prevent urine leakage.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A damless catheter condom for fitting around a human penis having a shaft portion and a head portion, said damless catheter condom comprising:
   a tubular portion comprising a tubular wall and a tubular portion average diameter and a longitudinal axis, said tubular portion average diameter being sized to encircle and sealingly grip said shaft portion and said head portion,
   a walled end of said tubular portion,
   a discharge port in said walled end wherein said discharge port is offset in position from said longitudinal axis and toward a point on said tubular wall.

2. The damless condom of claim 1, wherein the portion of said condom between the end of the penis and said discharge port is formed of material which is stiffer than the condom material surrounding the penis for reducing condom kinking potential.

3. A male external catheter assembly for transporting and containing urine, comprising:
   a condom having a discharge end and having a discharge port at said discharge end,
   a discharge tube having a tube first end and a tube second end, said tube first end being sealingly secured to said condom discharge end,
   a urine receiving vessel at said tube second end,
   a garment having a condom passing opening,
   a condom masking sleeve having a sleeve first end and a sleeve second end, said sleeve first end being positioned adjacent to said condom passing opening and substantially surrounding said condom discharge end for concealing said condom,
   wherein said sleeve first end is removably attached to said condom passing opening with attachment means.

4. The male external catheter of claim 3, wherein said condom masking sleeve is colored to match a nearby item to be visually less conspicuous.

5. The male external catheter of claim 3, wherein said garment is a pair of trousers having a conventional trouser fly opening and wherein said condom passing opening is located below said conventional trouser fly opening location.

6. A male external catheter assembly for transporting and containing urine, comprising:
   a condom having a discharge end and having a discharge port at said discharge end,
   a discharge tube having a tube first end and a tube second end, said tube first end being sealingly secured to said condom discharge end,
   a urine receiving vessel at said tube second end,
   a port plug for inserting into said condom discharge port for preventing urine leakage,
   wherein said port plug is absorbent.

7. The male external catheter of claim 6, wherein said port plug is essentially elongated and conical.

8. The male external catheter of claim 6, wherein said port plug is formed of tissue paper.

9. The male external catheter of claim 8, wherein said port is formed of a sheet of tissue paper twisted into a conical shape.

10. The male external catheter of claim 6, wherein said port. plug is formed of cotton.

11. A method of male catheterization for a user wearing a garment having a condom passing opening, comprising the steps of:
fitting a condom having a discharge port onto the user's penis,
extending said condom through said condom passing opening,
extending a free end of a discharge tube extending from said discharge port to discharge urine into a urine collection vessel.

12. The method of claim 11, additionally comprising the step of:
placing a condom masking sleeve over said condom, outside said condom passing opening, to conceal said condom.

13. A male external catheter assembly for transporting and containing urine, comprising:
a condom having a discharge end and having a discharge port at said discharge end,
a discharge tube having a tube first end and a tube second end, said tube first end being sealingly secured to said condom discharge end,
a urine receiving vessel at said tube second end,
a garment having a condom passing opening and a cuff,
a condom masking sleeve having a sleeve first end and a sleeve second end, said sleeve first end being positioned adjacent to said condom passing opening and substantially surrounding said condom discharge end for concealing said condom,
strap means for holding said garment cuff in position wherein said cuff encircles a leg of a user of said apparatus, comprising a strap for wrapping around the end of said leg, said strap having two strap ends connected to opposing points on said cuff, for preventing said garment from riding up on said leg as a result of wearing said apparatus.

14. The apparatus of claim 13, wherein at least one said end is secured to said cuff at one said point with clip means.

15. A male external catheter assembly for transporting and containing urine, comprising:
a condom having a discharge end hand having a discharge port at said discharge end,
a discharge tube having a tube first end and a tube second end, said tube first end being sealingly secured to said condom discharge end,
a urine receiving vessel at said tube second end,
a garment having a condom passing opening,
a condom masking sleeve having a sleeve first end and a sleeve second end, said sleeve first end being positioned adjacent to said condom passing opening and substantially surrounding said condom discharge end for concealing said condom,
wherein said condom masking sleeve comprises a condom inspection slit.

16. The male external catheter of claim 15, wherein said inspection slit extends essentially axially from said sleeve second end toward said sleeve first end.

17. The male external catheter of claim 15, wherein said sleeve first end is removably attached to said condom passing opening with attachment means.

18. The male external catheter of claim 15, wherein said sleeve first end is permanently attached to said condom passing opening with attachment means.

* * * * *